(12) United States Patent
Park et al.

(10) Patent No.: US 11,980,610 B2
(45) Date of Patent: May 14, 2024

(54) ORAL SOLID DOSAGE FORM COMPOSITION HAVING IMPROVED DISINTEGRATION AND PREPARATION METHOD THEREFOR

(71) Applicant: SAMYANG HOLDINGS CORPORATION, Seoul (KR)

(72) Inventors: Sang Yeob Park, Daejeon (KR); Hye Jung Lim, Daejeon (KR); Jae Young Lee, Seongnam-si (KR); Min Hyo Seo, Yongin-si (KR); Sa Won Lee, Seongnam-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 0 days.

(21) Appl. No.: 16/760,302

(22) PCT Filed: Oct. 30, 2018

(86) PCT No.: PCT/KR2018/013034
§ 371 (c)(1),
(2) Date: Apr. 29, 2020

(87) PCT Pub. No.: WO2019/088669
PCT Pub. Date: May 9, 2019

(65) Prior Publication Data
US 2020/0261426 A1    Aug. 20, 2020

(30) Foreign Application Priority Data
Oct. 31, 2017    (KR) ........................ 10-2017-0144139

(51) Int. Cl.
| | | |
|---|---|---|
| *A61K 31/436* | (2006.01) | |
| *A61K 9/00* | (2006.01) | |
| *A61K 31/192* | (2006.01) | |
| *A61K 31/366* | (2006.01) | |
| *A61K 31/4025* | (2006.01) | |
| *A61K 31/415* | (2006.01) | |
| *A61K 31/4178* | (2006.01) | |
| *A61K 31/44* | (2006.01) | |
| *A61K 31/47* | (2006.01) | |
| *A61K 31/501* | (2006.01) | |
| *A61K 31/502* | (2006.01) | |
| *A61K 31/5025* | (2006.01) | |
| *A61K 31/506* | (2006.01) | |
| *A61K 47/32* | (2006.01) | |

(52) U.S. Cl.
CPC .......... *A61K 31/436* (2013.01); *A61K 9/0053* (2013.01); *A61K 31/192* (2013.01); *A61K 31/366* (2013.01); *A61K 31/4025* (2013.01); *A61K 31/415* (2013.01); *A61K 31/4178* (2013.01); *A61K 31/44* (2013.01); *A61K 31/47* (2013.01); *A61K 31/501* (2013.01); *A61K 31/502* (2013.01); *A61K 31/5025* (2013.01); *A61K 31/506* (2013.01); *A61K 47/32* (2013.01)

(58) Field of Classification Search
CPC .................................................... A61K 31/436
See application file for complete search history.

(56) References Cited

U.S. PATENT DOCUMENTS

| | | | |
|---|---|---|---|
| 9,693,981 B2* | 7/2017 | Masri ................... | A61K 9/4808 |
| 2002/0031547 A1* | 3/2002 | Takagi ................. | A61K 9/2022 |
| | | | 424/464 |
| 2011/0020455 A1 | 1/2011 | Yoshida et al. | |
| 2011/0071169 A1* | 3/2011 | Huang ................... | A61P 35/00 |
| | | | 544/293 |

FOREIGN PATENT DOCUMENTS

| | | |
|---|---|---|
| CN | 102319251 A | 1/2012 |
| KR | 10-2000-0062327 A | 10/2000 |
| KR | 10-2009-0004280 A | 1/2009 |
| KR | 10-2009-0131584 A | 12/2009 |
| KR | 10-2013-0009906 A | 1/2013 |
| WO | WO 02/069932 A1 | 9/2002 |
| WO | WO 2004/006904 A1 | 1/2004 |
| WO | WO 2009/113522 A1 | 9/2009 |

OTHER PUBLICATIONS

Priemel, European Journal of Pharmaceutics and Biopharmaceutics vol. 85, Issue 3, Part B, Nov. 2013, pp. 1259-1265.*
Nokhodchi, BioImpacts, 2012, 2(4), 175-187.*
Patra, Future Journal of Pharmaceutical Sciences vol. 3, Issue 1, Jun. 2017, pp. 33-45.*
Choi, Pharmazie 75 (2020), 13-17.*
"Scientific Discussion, EMEA, 2006, European Medicines Agency." ("EMEA").*
International Search Report (PCT/ISA/210) issued in PCT/KR2018/013034, dated Feb. 28, 2019.
Extended European Search Report for European Application No. 18872612.9, dated Jul. 15, 2021.
Hughey et al., "The use of inorganic salts to improve the dissolution characteristics of tablets containing Soluplus-based solid dispersions," European Journal of Pharmaceutical Sciences, vol. 48, No. 4, 2013 (Available online Jan. 21, 2013), pp. 758-766.

* cited by examiner

*Primary Examiner* — Nizal S Chandrakumar
(74) *Attorney, Agent, or Firm* — Birch, Stewart, Kolasch & Birch, LLP

(57) ABSTRACT

Disclosed are an oral solid dosage form composition comprising an active ingredient and a solubilizing carrier wherein a foaming ingredient is used to improve disintegration, dispersion or dissolution, and a preparation method therefor.

10 Claims, No Drawings

ORAL SOLID DOSAGE FORM COMPOSITION HAVING IMPROVED DISINTEGRATION AND PREPARATION METHOD THEREFOR

TECHNICAL FIELD

The present invention relates to an oral solid formulation composition, in which a formulation has improved disintegration, dispersion or dissolution, comprising an active ingredient and a solubilizing carrier, and a method for preparing the same.

BACKGROUND ART

Polymeric materials are used in various ways to prepare oral solid formulations. In particular, various polymer materials have been used to impart properties such as improved stability of the active ingredient, amorphization of the crystalline form, improved solubility, improved absorption, site-specific delivery such as gastric retention or enteric formulations or large intestine delivery, sustained release, etc. Among them, a water-soluble or gastric-soluble polymer is used as a solubilizing carrier for the purpose of improving stability of the active ingredient, amorphization, improving solubility, improving absorption, etc., and is prepared in the form of a solid dispersion. Since solid dispersions often have a delay in disintegration, dispersion or dissolution in the finished product, various methods have been applied to prevent disintegration, dispersion, or dissolution from being delayed in formulations utilizing the solid dispersion.

Disintegrants and super disintegrants are known to prevent the delay of the disintegration, dispersion or dissolution of oral solid formulations. However, when a solid dispersion is contained, it is often difficult to see a large improvement by using a small amount of disintegrant and super disintegrant. In this case, the amount of the diluent is increased, and the size of the whole formulations is inevitably increased.

Therefore, in order to increase the patient's medication convenience and medication compliance, it is necessary to prevent the delay of the disintegration, dispersion or dissolution without increasing the size of the formulation.

CONTENTS OF THE INVENTION

Problems to be Solved

The purpose of the present invention is to provide an oral solid formulation composition, in which a formulation has improved disintegration, dispersion or dissolution, comprising an active ingredient and a water-soluble or gastric-soluble polymer as a solubilizing carrier.

Another purpose of the present invention is to provide a method for preparing an oral solid formulation composition, in which a formulation has improved disintegration, dispersion or dissolution, comprising an active ingredient and a water-soluble or gastric-soluble polymer as a solubilizing carrier.

Technical Means

In order to achieve the technical purpose, in the first aspect, the present invention provides an oral solid formulation composition comprising a mixture comprising an active ingredient and a water-soluble or gastric-soluble polymer as a solubilizing carrier, and a foaming component as a disintegration promoter.

In another aspect, the present invention provides a method for preparing an oral solid formulation composition comprising: (1) a step of preparing a mixture comprising an active ingredient and a water-soluble or gastric-soluble polymer as a solubilizing carrier; and (2) a step of adding a foaming component as a disintegration promoter to the mixture.

Effect of the Invention

The oral solid formulation composition of the present invention, in which a formulation has improved disintegration, dispersion or dissolution, comprising an active ingredient and a water-soluble or gastric-soluble polymer as a solubilizing carrier, not only can prevent the delay of disintegration of the oral solid formulation due to the polymer material, but also minimize the amount of additives used for disintegration. Thus, it can improve the medication adherence by minimizing the patient discomfort due to the size of the final formulation.

CONCRETE MODE FOR CARRYING OUT THE INVENTION

Definition of Terms

Unless otherwise expressly stated, some terms used throughout this specification may be defined as follows.

Unless specifically stated throughout this specification, "comprise" or "contain" refers to the comprisal any component without particular limitations, and it is not to be construed as excluding the addition of other components.

In addition, "active ingredient" may be a drug (base drug without a separate salt), a pharmaceutically acceptable salt of the drug, isomer of the drug or a mixture thereof.

Finding a Solution

The present inventors have made great efforts to improve the disintegration of oral solid formulations and found a composition that does not delay the release of drugs, has good physical properties and allows for smooth manufacturing and low weight formulations since disintegration, dispersion or dissolution is not delayed without significantly increasing the size of the final formulation when using foaming material.

DETAILED DESCRIPTION

The present invention provides an oral solid formulation composition, in which a formulation has improved disintegration, dispersion or dissolution, comprising a physiologically active ingredient and a polymer material and a method for preparing the same.

Active Ingredient

The active ingredient may comprise one or more selected from the group consisting of drugs, pharmaceutically acceptable salts of drugs and isomers of drugs.

In the present invention, as the active ingredient, for example, those selected from organic compounds, organometallic compounds, natural extracts, proteins and combinations thereof that exhibit physiological activity in pharmaceuticals, functional foods, cosmetics and the like can be used. In the above-mentioned active ingredient, there is no particular limitation on its properties at room temperature such as a solid phase or a liquid phase or its electrical properties such as neutral or ionic properties.

According to certain embodiments of the present invention, the active ingredient includes, but is not limited to, for example, anticancer agents, antifungal agents, psychiatric agents such as analgesics, consciousness level-altering agents such as anesthetic agents or hypnotics, nonsteroidal antiinflammatory agents, anthelminthics, antiacne agents, antianginal agents, antiarrhythmic agents, anti-asthma agents, antibacterial agents, anti-benign prostatic hypertrophy agents, anticoagulants, antidepressants, antidiabetics, antiemetics, antiepileptics, antigout agents, antihypertensive agents, antiinflammatory agents, antimalarials, antimigraine agents, antimuscarinic agents, antineoplastic agents, anti-obesity agents, antiosteoporosis agents, antiparkinsonian agents, antiproliferative agents, antiprotozoal agents, antithyroid agents, antitussive agent, anti-urinary incontinence agents, antiviral agents, anxiolytic agents, appetite suppressants, beta-blockers, cardiac inotropic agents, chemotherapeutic drugs, cognition enhancers, contraceptives, corticosteroids, Cox-2 inhibitors, diuretics, erectile dysfunction improvement agents, expectorants, gastrointestinal agents, histamine receptor antagonists, immunosuppressants, keratolytics, lipid regulating agents, leukotriene inhibitors, macrolides, muscle relaxants, neuroleptics, nutritional agents, opioid analgesics, protease inhibitors, or sedatives as a physiologically active substance, salt, isomer, ester, ether or other derivative thereof.

There are no particular restrictions on the active ingredients applicable to the present invention. For example, the active ingredient that can be formulated into the composition of the present invention may be one or more selected from the group consisting of the following components, but is not limited to:

Antipsychotic drugs such as chlorpromazine, thioridazine, loxapine, molindone, clozapine, olanzapine, quetiapine, risperidone, ziprasidone, fluphenazine, haloperidol, perphenazine, trifluoperazine, pimozide, aripiprazole, prochlorperazine, thioticene, paliperidone, etc.;

Antidepressants such as mirtazapine, bupropion, amoxapine, phenelzine, tranylcypromine, citalopram, fluorcetin, fluvoxamine, paroxetine, sertraline, venlafaxine, maprotiline, trazodone, nefazodone, amitriptyline, clomipramine, desipramine, decepine, imipramine, nortriptyline, protriptyline, trimipramine, etc.;

Neurodegenerative disease drugs such as amantadine, benztropine mesylate, carbidopa and levodopa, donepezil, bromocriptine, pergolide, pramipexole, ropinirole, etc.;

Anti-ADHD (attention deficit hyperactivity disorder) drugs such as methylphenidate, atomoxetine, etc.;

Anticonvulsants such as pregabalin, lacosamide, carbamazepine, clonazepam, ethosuximide, felbamate, gabapentin, lamotrigine, levetiracetam, oxcarbazepine, phenobarbital, phenytoin, primidone, tiagabine, topiramate, valproic acid, divalproex sodium, zonisamide, etc.;

Anti-anxiety drugs, sedatives or hypnotics such as alprazolam, lorazepam, oxazepam, chlordiazepoxide, clorazepate, diazepam, halazepam, midazolam, triazolam, zaleplon, zolpidem, estazolam, temazepam, flurazepam, quazepam, meprobamate, phenobarbital, chloral hydrate, etchlorbinol, glutethimide, pentobarbital, secobarbital, etc.;

Erectile dysfunction drugs such as sildenafil, vardenafil, alprostadil, tadalafil, mirodenafil, udenafil, etc.;

Immunosuppressive agents such as azathioprine, cyclosporine, mycophenolate mofetil, sirolimus, tacrolimus, everolimus, etc.;

Antihypertensive drugs such as doxazosin mesylate, prazosin hydrochloride, terazosin hydrochloride, benazepril, captopril, clonidine hydrochloride, enalapril, hydralazine hydrochloride, labetalol hydrochloride, losartan potassium, methyldopa hydrochloride, minoxidil, moexipril, trandolapril, candesartan, irbesartan, losartan, telmisartan, valsartan, guanabenz acetate, guanadrel sulfate, guanfacine hydrochloride, reserpine, etc.;

Beta-adrenergic blocking drugs such as acebutolol, atenolol, betaxolol, bisoprolol, carteolol, carvedilol, labetalol, metoprolol, nadolol, penbutolol, pindolol, propranolol, sotalol, timolol, etc.;

Calcium-channel blockers such as amlodipine, bepridil, diltiazem, felodipine, isradipine, nicardipine, nifedipine, nimodipine, nisoldipine, verapamil, etc.;

Hypolipidemic drugs such as fenofibrate, gemfibrozil, niacin, atorvastatin, fluvastatin, lovastatin, pravastatin, simvastatin, etc.;

Gastrointestinal motility drugs such as mosapride, itopride, domperidone, trimebutine, metoclopramide, bisacodyl, diphenoxylate hydrochloride and atropine sulfate, docusate salt, loperamide, magnesium salt, metoclopramide, ursodiol, etc.;

Coagulants and anticoagulants such as clopidogrel bisulfate, phytonadione, ticlopidine, warfarin sodium, etc.;

Vasodilators such as limaprost, beraprost, and sarpogrelate;

Antimigraine drugs such as almotriptan, ergotamine tartrate, frovatriptan, methysergide maleate, sumatriptan succinate, zolmitriptan, etc.;

Antirheumatic drugs such as auranofin, azathioprine, cyclosporine, hydroxychloroquine sulfate, leflunomide, methotrexate, penicillamine, sulfasalazine, etc.;

Non-steroidal anti-inflammatory drugs such as acetaminophen, aspirin, diclofenac, etodolac, fenoprofen, ibuprofen, ketoprofen, naproxen, indomethacin, ketorolac, sulindac, tolmetin, meclofenamate, mefenamic acid, nabumetone, meloxicam, piroxicam, celecoxib, rofecoxib, etc.;

Opioids such as buprenorphine, codeine, fentanyl, hydrocodone, hydromorphone, levorphanol, meperidine, morphine, oxycodone, pentazocine, propoxyphene, etc.;

Non-drug analgesics such as tramadol and tapentadol;

Anticancer agents such as imatinib, erlotinib, sunitinib, sorafenib, lapatinib, gefitinib, dasatinib, lenalidomide, nilotinib, crizotinib, pazopanib, vandetanib, axitinib, regorafenib, afatinib, vemurafenib, ruxolitinib, temozolomide, radotinib, everolimus, pomalidomide, olaparib, enzalutamide, palbociclib, osimertinib, ibrutinib, lenvatinib, ceritinib, bosutinib, cabozantinib, dabrafenib, ponatinib, etc.;

Anti-mycobacterial drugs such as aminosalicylic acid salt, clofazimine, cycloserine, ethionamide, rifabutin, etc.;

Antiparasitic drugs such as albendazole, ivermectin, mebendazole, praziquantel, etc.;

Antiviral drugs such as valacyclovir, didanosine, famciclovir, valganciclovir, indinavir, lamivudine, nelfinavir mesylate, nevirapine, ritonavir, stavudine, oseltamivir phosphate, etc.;

Beta-lactams such as amoxicillin, amoxicillin and potassium clavulanate, ampicillin, cefuroxime sodium, cefuroxime axetil, penicillin G and Y salts, cefditoren, cefixime, cloxacillin sodium, dicloxacillin sodium, etc.;

Macrolide antibiotics such as erythromycin estolate, erythromycin ethylsuccinate, erythromycin stearate, etc.;

Fluoroquinolone such as ciprofloxacin and enoxacin, etc.;

Tetracyclines such as demeclocycline hydrochloride, doxycycline calcium, tetracycline, tetracycline hydrochloride, etc.;

Alkylating agents such as altretamine, busulfan, chlorambucil, melphalan, cyclophosphamide, procarbazine hydrochloride, temozolomide, etc.;

Anti-metabolites such as methotrexate, mercaptopurine, thioguanine, etc.;

Hormonal drugs and antagonists such as bicalutamide, flutamide, nilutamide, aminoglutethimide, anastrozole, exemestane, letrozole, tamoxifen citrate, toremifene citrate, etc.;

Mitotic inhibitors such as etoposide phosphate, etc.;

Arrhythmia drugs such as amiodarone hydrochloride, digoxin, disopyramide phosphate, dofetilide, flecainide acetate, mexiletine hydrochloride, moricizine hydrochloride, procainamide hydrochloride, propafenone hydrochloride, quinidine sulfate, quinidine gluconate, sotalol hydrochloride, tocainide, etc.;

Nitrates such as isosorbide dinitrate, nitroglycerin, sodium nitroprusside, etc.;

Glaucoma eye drops drugs such as acetazolamide, dichlorphenamide, methazolamide, etc.;

Drugs for the treatment of acid-pepsin, such as aluminum carbonate, aluminum hydroxide, magnesium hydroxide, sodium bicarbonate, calcium carbonate, magaldrate, etc.;

Bismuth salt, cimetidine, famotidine, nizatidine, ranitidine, misoprostol, lansoprazole, omeprazole, pantoprazole, rabeprazole, sucralfate, etc.;

Antiemetics such as buclizine, cyclizine, dimenhydrinate, diphenhydramine, meclizine, dronabinol, chlorpromazine, perphenazine, prochlorperazine, promethazine, thiethylperazine, triflupromazine, dolasetron, granisetron, ondansetron, dexamethasone, lorazepam, granisetron, ramosetron, aprepitant, etc.;

Hematopoietic drugs such as iron salts, etc.;

Adrenaline hormones such as cortisone, hydrocortisone, methylprednisolone, prednisone, triamcinolone, betamethasone, dexamethasone, fludrocorti sone, etc.;

Antidiabetic drugs such as acarbose, metformin, nateglinide, repaglinide, acetohexamide, chlorpropamide, tolazamide, tolbutamide, glimepiride, glipizide, glyburide, pioglitazone, rosiglitazone, etc.;

Contraceptives such as norethindrone, norgestrel, levonorgestrel, etc.;

Female sex hormones such as estradiol and its esters, estrogens, estropipate, medroxyprogesterone, mifepristone, norethindrone acetate, progesterone, raloxyphen, etc.;

Thyroid and antithyroid drugs such as iodide, levothyroxine sodium, liothyronine sodium, liotrix, methimazole, propylthiouracil, etc.;

Diuretics such as amiloride hydrochloride, bumetanide, ethacrynic acid, furosemide, torsemide, hydrochlorothiazide, chlorothiazide, chlorthalidone, indapamide, metolazone, polythiazide, quinethazone, tricomethiazide, spironolactone, triamterene, etc.;

Electrolytic materials such as chelated magnesium, magnesium chloride, magnesium hydroxide, magnesium oxide, potassium salts, etc.;

Gout treatment drugs such as allopurinol, colchicine, probenecid, sulfinpyrazone, etc.;

Treatments for asthma such as albuterol sulfate, montelukast sodium, theophylline, zileuton, etc.;

Antihistamines such as acrivastine, azatadine, brompheniramine maleate, carbinoxamine maleate, cetirizine hydrochloride, chlorpheniramine maleate, diphenhydramine hydrochloride, clemastine fumarate, cyproheptadine hydrochloride, fexofenadine, hydroxyzine, loratadine, desloratadine, etc.;

Cough suppression drugs or cold treatment drugs such as dextromethorphan hydrobromide, guaifenesin, pseudoephedrine hydrochloride, etc.; and Health functional food.

The active ingredient may be comprised in the amount of 0.5 to 70% by weight, preferably 1 to 60% by weight, more preferably 2 to 55% by weight, most preferably 3 to 50% by weight, based on the total weight of the composition.

Polymers

The polymer in the present invention refers to a water-soluble or gastric-soluble polymer used as a solubilizing carrier.

The term "solubilizing carrier" is a concept encompassing carrier components used for the purpose of improving stability of the active ingredient, amorphization, improving solubility and improving absorption, etc.

The polymer used as the solubilizing carrier may be used in an amount of 7 to 70% by weight, preferably 10 to 60% by weight, more preferably 12 to 50% by weight based on the total weight of the composition.

The polymer usable in the present invention is used in pharmaceuticals, foods and/or cosmetics, and there is no particular limitation on its properties (e.g., liquid phase, wax or solid phase, etc.) at room temperature.

Specific examples of the polymers are selected from gelatin, casein, dextran, gum acacia, tragacanth, polyethylene glycols, carboxymethyl cellulose, hydroxypropyl cellulose, hydroxypropyl methylcellulose, methyl cellulose, hydroxyethyl cellulose, hydroxypropyl methyl cellulose phthalate, hydroxypropyl methylcellulose acetate succinate, methylcellulose noncrystalline cellulose, polyvinyl alcohol, polyvinypyrrolidone, poloxamer, polymethacrylate copolymer, lysozyme, albumin, polyacrylic acid and combinations thereof, but they are not limited to this. Preferred polymers include hydroxypropyl methylcellulose, polyvinylpyrrolidone, poloxamer, polymethacrylate copolymers, hydroxypropyl cellulose or combinations thereof.

Finished Product Using Active Ingredients and Polymers

In the preparation of an oral composition, the finished product can be formulated in various ways.

The oral composition of the present invention may preferably be in the form of a solid oral formulation, particularly a tablet or capsule.

When preparing a finished product using a polymer for the purpose of improving stability of the active ingredient, amorphization of the crystalline form, improving solubility and improving absorption, disintegration, dispersion, and dissolution are often delayed in the finished product. In the method of using a polymer, a polymer can be present in the finished product by using a solid dispersion or the granulated form or directly mixing the polymer, and the method is not limited in the present invention.

In the case of a solid dispersion, it can be prepared in various ways, such as spray drying, dissolving and drying under reduced pressure, or precipitation. Examples of granulation include wet granules and dry granules. For wet granulation, a high-speed mixer or a fluid bed granulator may be used, and for dry granulation, a roller compactor or an extruder, etc. may be used.

Disintegration Promoter—Foaming Component

Disintegration properties, dispersion properties, dissolution properties, and dissolution-retention properties in aqueous solutions, etc., should be maintained even in the finished product. However, the polymers are highly viscous and have strong bonding strength, and thus may play a role of delaying disintegration, dispersion and dissolution of the finished product. In particular, hypromellose (=hydroxypropyl methylcellulose) or povidone (=polyvinylpyrrolidone) is a hydrophilic polymer that has a property of absorbing water well. When a tablet made of a hydrophilic polymer, an active ingredient and other excipients meets water, the polymer hydrates to form a swelling surface, and at the same time, forms a glassy layer in the tablet that was in a dry core state. Subsequently, as time passes, the layer becomes a gel layer to form a diffusion layer, and the active ingredient molecules are gradually released to the external media through the diffusion layer. After more time, the tablets form an erosion surface where erosion occurs on the surface of the tablets by external stimuli such as peristaltic movements of the intestine. Due to this process, the active ingredient exhibits a delay in release. The polymer such as 2280 and 2910, has a higher delay effect.

However, in most cases, the formulation must disintegrate rapidly in the body, so that the active ingredient reaches the final dissolution rate in a short time. This is because in the case of an active ingredient in which solubility decreases as the pH increases, it is necessary to maintain the highest concentration in the upper part of the gastrointestinal tract to promote absorption. Therefore, the polymer used to impart the function may be a barrier to improvement of absorption due to the delayed release of the active ingredient.

In particular, when making a finished product in the form of a tablet, the disintegration of the tablet formed by tableting may be delayed by the polymer. In addition, even if disintegration occurs, dispersion or dissolution in the form of granules or clumps can be delayed by polymers.

When tablets containing high-viscosity hydrophilic polymers such as hypromellose contact with water, the polymer on the surface is hydrated to form a film to prevent moisture penetration on the inside. In order to prevent this phenomenon, a method such as the use of a disintegrant or a large amount of excipients can be applied.

When a disintegrant is used, water may be drawn into the tablet to promote disintegration, dispersion and dissolution of the formulation through wetting through the capillary action or swelling of the disintegrant itself.

In addition, when using a large amount of diluent, the polymers can be separated from each other to prevent disintegration delay.

However, when a large amount of disintegrant is used, the final formulation may be sensitive to moisture, resulting in deterioration in stability. And when a large amount of diluent is used, there is a disadvantage in that the final formulation becomes large.

Accordingly, the tablet composition was designed to promote disintegration by preventing the formation of a gel layer by spacing the gap between the polymer particles with physical force at the moment of contact with water. For this purpose, it was proposed to use a foaming component.

In one embodiment, sodium hydrogen carbonate, used as a pH adjuster and antacid, generates $CO_2$ gas in an acidic solution and rapidly expands the volume of the tablet due to the pressure change generated at this time, whereby it can promote the penetration of moisture on the tablet and disintegration.

In one embodiment, the chemical reaction of the tablet surface containing $NaHCO_3$ under gastric fluid conditions is as follows:

$$NaHCO_3(s) + HCl(aq) \rightarrow NaCl(aq) + H_2O(l) + CO_2(g)$$

As an additive exhibiting foamability, the formulation of the present invention may include a foaming agent or an acidifying agent.

As the foaming agent, an alkali metal carbonate may be used, preferably sodium carbonate, sodium hydrogen carbonate (sodium bicarbonate), potassium carbonate or potassium hydrogen carbonate may be used alone or in combination, and most preferably sodium hydrogen carbonate may be used. It is preferred that the composition of the present invention comprises 10 to 200 parts by weight of the foaming agent based on 100 parts by weight of the polymer. If the foaming agent is comprised in the amount of less than 10 parts by weight, the foaming performance may decrease. If the amount of the foaming agent exceeds 200 parts by weight, the preparation of the formulation may be difficult due to the decrease in the content of other components, and due to excessive foam performance, bubbles can occur even in small amounts of water exposure during distribution and storage, indicating a decrease in stability. The foaming agent may be used in an amount of preferably 20 to 170 parts by weight, more preferably 30 to 150 parts by weight, and most preferably 50 to 120 parts by weight based on 100 parts by weight of the polymer.

As the acidifying agent, citric acid, succinic acid, tartaric acid, ascorbic acid, fumaric acid, malic acid, acetylsalicylic acid and nicotinic acid may be used alone or in combination, and most preferably citric acid or tartaric acid may be used. In the composition of the present invention, the acidifying agent may preferably be comprised in an amount of 0 to 200 parts by weight, more preferably 0 to 150 parts by weight, and most preferably 0 to 100 parts by weight based on 100 parts by weight of the foaming agent. When the acidifying agent is not added, gastric acid plays a role, and when the acidifying agent is comprised in the amount of exceeding 200 parts by weight, the content of other ingredients is lowered, and a problem may arise in that the hardness of the formulation is lowered.

When the acidifying agent is comprised in the formulation, the formulation may draws moisture in the air during manufacturing or storage, and it may react with moisture and foam. Thus, it is necessary to block moisture during processing or storage.

However, since oral tablets are directly exposed to strong acidic gastric juice after taking the drug, it is preferable to use a foaming agent (for example, sodium hydrogen carbonate) only as an additive without using an acidifying agent.

The composition of the present invention may comprise other additional components in addition to sorafenib nanoparticles. Examples of other additional components include dissolution aids, diluents, disintegrants, lubricants and coating agents.

A polymer or a surfactant may be used as the dissolution aid. Preferably, a polymethacrylate copolymer can be used. The polymethacrylate copolymer is preferably a cationic polymer with dimethyl-aminoethyl methacrylate as a functional group, more preferably poly(butylmethacrylate-co-(2-dimethylaminoethyl)methacrylate-co-methylmethacrylate).

The polymethacrylate copolymer may have a weight average molecular weight of 3,000 to 200,000, preferably 5,000 to 150,000, more preferably 10,000 to 100,000, and even more preferably 20,000 to 80,000 g/mole. If the weight average molecular weight is less than 3,000 g/mole, the water solubility improvement effect may be low. If the weight average molecular weight exceeds 200,000 g/mole, disintegration may be delayed.

The state of the polymethacrylate copolymer is not particularly limited, but may be in the form of granules or powder.

As a specific example, the polymethacrylate copolymer may be Eudragit® E PO (Evonik, Germany) or Eudragit® E 100 (Evonik, Germany). As a specific example, the weight average molecular weight of the polymethacrylate copolymer may be about 47,000 g/mole.

The polymethacrylate copolymer may be used in an amount of 0.05 to 5 parts by weight, preferably 0.1 to 4 parts by weight, more preferably 0.2 to 3 parts by weight, based on 1 part by weight of the active ingredient. When the amount of the polymethacrylate copolymer is less than the above-mentioned lower limit, the improvement in the water solubility and bioavailability of the active ingredient is insignificant, and the effect may be deteriorated. If the amount exceeds the above-mentioned upper limit, the formulation (e.g., tablet) becomes too large, which may cause discomfort when the patient is taking it.

The diluent may be one or more selected from the group consisting of, for example, lactose (anhydride or hydrate, for example monohydrate), cellulose powder, microcrystalline cellulose, silicified microcrystalline cellulose, starch, dicalcium phosphate, tricalcium phosphate, magnesium trisilicate, mannitol, maltitol, sorbitol, xylitol, lactose, dextrose, maltose, sucrose, glucose, fructose, maltodextrin and mixtures thereof, but it is not limited thereto. Preferably lactose, microcrystalline cellulose or mixtures thereof can be selected. Most preferably, a mixture of starch, lactose and microcrystalline cellulose can be selected. Diluents may also act as binders.

The diluent may be used in an amount of 0.1 to 80 parts by weight, preferably 1 to 65 parts by weight, and more preferably 2 to 50 parts by weight, based on 100 parts by weight of the total formulation (e.g., tablet). If the amount of the diluent is less than the above-mentioned lower limit, it may be difficult to prepare a formulation due to lowering of tabletting properties. If the amount of the diluent exceeds the above-mentioned upper limit, the formulation becomes too large, which may cause discomfort when the patient is taking it.

The disintegrant may be one or more selected from the group consisting of, for example, croscarmellose sodium (CrosCMC-Na), carboxymethylcellulose, crospovidone (crosslinked polyvinylpyrrolidone), L-HPC (low-substituted hydroxypropylcellulose), starch (wheat, rice, corn or potato starch), sodium carboxymethyl starch, sodium glycolate of potato starch, partially hydrolyzed starch and mixtures thereof, but it is not limited thereto. Preferably, it may be croscarmellose sodium (CrosCMC-Na) or L-HPC (low-substituted hydroxypropylcellulose) or a mixture thereof.

The disintegrant may be used in an amount of 1 to 30 parts by weight, preferably 2 to 20 parts by weight, based on 100 parts by weight of the total formulation (e.g., tablet). If the amount of the disintegrant is less than the above-mentioned lower limit, there may be a problem of delaying dissolution rate due to the disintegration rate delay. If the amount of the disintegrant exceeds the above-mentioned upper limit, there may be problems in productivity such as tabletting disorder.

The lubricant may be one or more selected from the group consisting of, for example, magnesium stearate, fumaric acid, stearic acid, calcium stearate, sodium stearyl fumarate, polyethylene glycol, starch (wheat, rice, corn or potato starch), talc, highly dispersed (colloidal) silica, magnesium oxide, magnesium carbonate, glyceryl behenate, glyceryl monostearate, silicon dioxide, calcium silicate, magnesium silicate and mixtures thereof, but it is not limited thereto. Preferably, it may be magnesium stearate.

The lubricant may be used, for example, in an amount of 0.1 to 3 parts by weight, preferably in an amount of 0.2 to 3 parts by weight, more preferably in an amount of 0.5 to 2 parts by weight, based on 100 parts by weight of the total formulation (e.g., tablet). If the amount of the lubricant is less than the above-mentioned lower limit, there may be problems in productivity such as tableting disorder. If the amount of the lubricant exceeds the above-mentioned upper limit, there may be a problem in dissolution delay or productivity.

The coating agent may be a hydrophilic polymer, and one or more selected from the group consisting of, for example, polyvinylpyrrolidone (PVP), polyvinyl acetate (PVA), hydroxypropylmethylcellulose (HPMC), carboxymethylcellulose (sodium salt and calcium salt), ethylcellulose, methylcellulose, hydroxyethylcellulose, ethylhydroxyethylcellulose, hydroxypropylcellulose (HPC), L-HPC (low-substituted HPC), polyvinyl alcohol, polymer of acrylic acid and salts thereof, vinylpyrrolidone-vinyl acetate copolymers (e.g. Kollidon® VA64, BASF), Polycoat IR, gelatin, guar rubber, partially hydrolyzed starch, alginate, xanthan and mixtures thereof, but it is not limited thereto. Preferably, it may be polyvinyl acetate (PVA), hydroxypropyl methylcellulose (HPMC) or polycoat IR.

The coating agent may be used in an amount of 0.2 to 15 parts by weight, preferably 0.5 to 10 parts by weight, more preferably 1 to 7 parts by weight, based on 100 parts by weight of the tablet before coating (uncoated tablet). If the amount of the coating agent is less than the above-mentioned lower limit, there may be a problem that a part of the entire surface of the uncoated tablet is not covered with the coating agent. If the amount of the coating agent exceeds the above-mentioned upper limit, there may be an excessive delay in the dissolution rate.

As described above, in the process of manufacturing the coated tablet, various biologically inert components can be further used for additional purposes such as coating efficiency, stability of the active ingredient, appearance, color, protection, maintenance, bonding, performance improvement, and manufacturing process improvement.

According to one embodiment, the biologically inert components that may be further comprised in the coating layer, may be one or more selected from the group consisting of plasticizers, lubricants, colorants, flavoring agents, surfactants, stabilizers, antioxidants, foaming agents, antifoaming agents, desiccants (e.g., paraffin, wax), etc.

For example, the plasticizer may be comprised in an amount of 100% by weight or less (e.g., 0.1 to 100% by weight), specifically 50% by weight or less (e.g., 0.1 to 50% by weight), more specifically 30% by weight or less (e.g., 0.1 to 30% by weight) based on the dry weight of the entire polymer used in each coating layer.

For example, the plasticizer may be one or more selected from the group consisting of triethyl citrate, dibutyl phthalate, diethyl phthalate, dibutyl sebacate, diethyl sebacate, tributyl citrate, acetyl triethyl citrate, acetyl triethyl citrate, propylene glycol, triacetin, polyethylene glycol, cetyl alcohol, stearyl alcohol and cetostearyl alcohol, but is not limited thereto.

For example, the lubricant may be comprised in an amount of 100% by weight or less (e.g., 0.1 to 100% by weight) based on the dry weight of the entire polymer used in each coating layer.

For example, the lubricant may be one or more selected from the group consisting of magnesium stearate, fumaric acid, stearic acid, calcium stearate, sodium stearyl fumarate, polyethylene glycol, starch (wheat, rice, corn or potato starch), talc, highly dispersed (colloidal) silica, magnesium oxide, magnesium carbonate, glyceryl behenate, glyceryl mono stearate, silicon dioxide, calcium silicate, magnesium silicate and mixtures thereof, but is not limited thereto.

In the tablet or capsule, various additives may be mixed to improve physical properties, manufacturability, compressibility, appearance, taste and drug stability of the tablet or capsule. The additives may include, for example, stabilizers, solubilizers, sweeteners, bitter medicine, pigments, wetting agents, fillers, surfactants, lubricants, buffers, adsorbents, binders, suspending agents, curing agents, antioxidants, brighteners, fragrance agents, flavoring agents, coating agents, wetting control agents, antifoaming agents, refreshing agents, chewing agents, antistatic agents, coloring agents, sugar agents, isotonic agents, emollients, emulsifiers, adhesives, thickeners, foaming agents, pH adjusting agents, excipients, dispersing agents, disintegrants, waterproofing agents, preservatives, conservants, dissolving aids, solvents, fluidizing agents and the like, but are not limited thereto and can be used as long as they are pharmaceutically acceptable.

Hereinafter, preferred embodiments are provided to facilitate understanding of the present invention. However, the following examples are only intended to illustrate the invention, and are not intended to limit the invention in any way.

EXAMPLES

Preparation Example 1. Preparation of Solid Dispersion: Tacrolimus

After dissolving or dispersing 0.5 g of hydroxypropylmethylcellulose (HPMC) and 0.5 g of tacrolimus in 35 g of ethanol, the mixture was evaporated and dried in a convection oven. Then, it was pulverized to about 300 µm or less using a mixer to prepare a solid dispersion.

Preparation Example 2. Preparation of Solid Dispersion: Tacrolimus 2.5 g of HPMC 2910 and 34.375 g of water were quantitatively mixed and completely dissolved while stirring to prevent foaming. 0.5 g of tacrolimus and 51.5625 g of ethanol were quantified and then mixed and stirred to dissolve completely. The tacrolimus solution and the HPMC aqueous solution were mixed homogeneously, and 0.825 g of talc was quantified and added to the mixture. Then stirring was continued to prevent precipitation, thereby preparing a coating solution.

The process air of the fluidized bed coating machine (GPCG1, GLATT) was adjusted to 44° C./0.17 bar and heated to maintain the temperature in the product chamber at 29-30° C. 10 g of microcrystalline cellulose (cp-102) was added to the fluidized bed coating machine, and the coating solution was sprayed into the product chamber at a jetting air velocity of 0.65 ml/min. As the coating progressed, the process air pressure was gradually increased from 0.17 bar to 0.25 bar and sprayed. After that, it was further dried for about 30 minutes to prepare a solid dispersion.

Preparation Example 3. Preparation of Solid Dispersion: Fenofibrate 20 g of polyethylene glycol 6000 (Macrogol 6000, Sanyo Chemical Industries, Japan) and 40 g of poloxamer 188 (Lutrol F68, BASF, Germany) were added to a beaker, heated to about 90° C., melted and mixed by stirring. After completely melting, 20 g of hydroxypropylmethylcellulose (Pharmacoat 606, ShinEtsu, Japan) was added to the previous melt solution and stirred to make it uniform. 20 g of fenofibrate was added thereto, and the mixture was stirred and melted. After complete melting and mixing, the mixture was spread out in a separate container for 4 hours to cool to room temperature.

The completely solidified lump was crushed to an appropriate size and pulverized into fine particles using an ERWEKA AR402 (ERWEKA GmbH, Germany) equipped with an 800 µm stainless steel sieve to obtain a solid dispersion.

Preparation Example 4. Preparation of Solid Dispersion: Fenofibrate 10 g of HPMC (2910 series, ShinEtsu Chemical, hereinafter the same) was mixed with 90 g of water and stirred to prepare a 10% w/w solution completely dissolved. 2 g of fenofibrate was mixed with 200 g of ethanol and stirred to dissolve completely. The two solutions were mixed and stirred to prepare a solution without precipitation. The ratio of fenofibrate to HPMC was 1:5 by weight (weight of fenofibrate: weight of HPMC).

The above solution was spray-dried with BUCHI's nozzle spray dryer (Mini spray dryer B-290, Buchi) at an injection air temperature of 90° C. and an injection volume of 3 mL/min to obtain a microsphere containing fenofibrate which is relatively spherical and has an average particle size of 50 µm.

Preparation Example 5. Preparation of Solid Dispersion: Fenofibrate 450 g of HPMC was mixed with 2550 g of water and stirred to prepare a 15% w/w solution completely dissolved. 90 g of fenofibrate was mixed with 5500 g of ethanol and stirred to dissolve completely. The two solutions were mixed and stirred to prepare a solution without precipitation. The ratio of fenofibrate to HPMC was 1:5 by weight.

The above solution was spray-dried with an atomizer-type spray dryer (DJE-003R, Dongjin Enterprise Co., Ltd.) at a spray temperature of 110° C., an injection volume of 45 mL/min and an atomizer speed of 3,500 rpm to obtain a microsphere containing fenofibrate which is relatively spherical and has an average particle size of 50 µm.

Preparation Example 6. Preparation of Solid Dispersion: Simvastatin

By mixing in the same manner as in Preparation Example 2 in the composition ratio as shown in the following Table 1, a clear mixed solution having a yellowish light was prepared, and the air bubbles were left to disappear.

TABLE 1

| Categories | Weight ratio | Amount (g) |
|---|---|---|
| HPMC | 5 | 300 |
| Water |  | 1,700 |
| Ethanol |  | 4,000 |
| Simvastatin | 1 | 60 |
|  |  | 6,060 |

The above solution was spray-dried with an atomizer-type spray dryer at a spray temperature of 100° C., an injection volume of 45 mL/min and an atomizer speed of 3,500 rpm to obtain a relatively spherical 50 µm-sized simvastatin microsphere in the form of a solid dispersion.

Preparation Example 7. Preparation of Solid Dispersion: Candesartan

By mixing in the same manner as in Preparation Example 2 in the composition ratio as shown in the following Table 2, a clear mixed solution having a yellowish light was prepared, and the air bubbles were left to disappear.

TABLE 2

| Categories | Weight ratio | Amount (g) |
|---|---|---|
| HPMC | 5 | 300 |
| Water |  | 1,700 |
| Ethanol |  | 4,000 |
| Candesartan | 1 | 60 |
|  |  | 6,060 |

The above solution was spray-dried with an atomizer-type spray dryer at a spray temperature of 100° C., an injection volume of 45 mL/min and an atomizer speed of 3,500 rpm to obtain a relatively spherical candesartan microsphere in the form of a solid dispersion. It was found that the prepared microspheres had a particle size of 50 µm or less in the form of a solid dispersion.

Preparation Example 8. Preparation of Solid Dispersion: Tacrolimus

By mixing in the same manner as in Preparation Example 2 in the composition ratio as shown in the following Table 3, a clear mixed solution having a yellowish light was prepared, and the air bubbles were left to disappear.

TABLE 3

| Categories | Weight ratio | Amount (g) |
|---|---|---|
| HPMC | 5 | 300 |
| Water |  | 1,700 |
| Ethanol |  | 4,000 |
| Tacrolimus | 1 | 60 |
|  |  | 6,060 |

The above solution was spray-dried with an atomizer-type spray dryer at a spray temperature of 100° C., an injection volume of 45 mL/min and an atomizer speed of 3,500 rpm to obtain a relatively spherical tacrolimus microsphere in the form of a solid dispersion. It was found that the prepared microspheres had a particle size of 50 µm or less in the form of a solid dispersion.

Preparation Example 9. Preparation of Solid Dispersion: Celecoxib 6 g of HPMC was mixed with 60 g of water and stirred to make a completely dissolved 10% w/w solution. 2 g of celecoxib and 2 g of poloxamer 188 were put into 200 g of ethanol and stirred and completely dissolved while heating at 40-50° C. The two solutions were mixed and stirred to prepare a solution without precipitation. The ratio of celecoxib:HPMC:poloxamer 188 was 1:3:1.

The above solution was spray-dried with GLATT's nozzle-type spray dryer (Mini Glatt) at an injection air temperature of 65-75° C. and an injection amount of 1-3 mL/min to obtain celecoxib-containing solid dispersion microspheres.

Preparation Example 10. Preparation of Solid Dispersion: Celecoxib 2 g of PVP K30 and 2 g of poloxamer 407 were added to a beaker with 60 ml of ethanol and stirred and completely dissolved while heating at 40-50° C. Then, it was confirmed that 2 g of celecoxib was further added to dissolve transparently. The ratio of celecoxib:PVP K30:poloxamer 407 was 1:1:1.

The above solution was spray-dried with GLATT's nozzle-type spray dryer (Mini Glatt) at an injection air temperature of 55-65° C. and an injection amount of 1-3 mL/min to obtain celecoxib-containing solid dispersion microspheres.

Preparation Example 11. Preparation of Solid Dispersion: Celecoxib 2 g of HPC-SSL and 2 g of poloxamer 407 were added to a beaker with 60 ml of ethanol and stirred and completely dissolved while heating at 40-50° C. Then, it was confirmed that 2 g of celecoxib was further added to dissolve transparently. The ratio of celecoxib:HPC-SSL:poloxamer 407 was 1:1:1.

The above solution was spray-dried with GLATT's nozzle-type spray dryer (Mini Glatt) at an injection air temperature of 65° C. and an injection amount of 1-3 mL/min to obtain celecoxib-containing solid dispersion microspheres.

Preparation Example 12. Preparation of Solid Dispersion: Celecoxib 240 g of HPC-SL, 240 g of PVP K 30 and 480 g of poloxamer 407 were added to a beaker with 14.4 L of ethanol and stirred and completely dissolved while heating at 40-50° C. Then, it was confirmed that 480 g of celecoxib was further added to dissolve transparently. The ratio of celecoxib:HPC-SL:PVP K30:poloxamer 407 was 1:0.5:0.5:1.

The above solution was spray-dried with an atomizer-type spray dryer at an injection air temperature of 55-65° C., an injection amount of 20-100 mL/min and an atomizer speed of 3,500-4,500 rpm.

Preparation Example 13. Preparation of Solid Dispersion: Imatinib

After completely dissolving 0.30 g of citric acid in 50 ml of purified water, 2 g of imatinib free base was added and dissolved. 0.25 g of polyvinylpyrrolidone K25 (Kollidon® 25, BASF, Germany) was completely dissolved in 50 ml of ethanol, added to the solution, and stirred to obtain a transparent liquid.

The completely dissolved and mixed solution was spray-dried with GLATT's nozzle type spray dryer (Mini Glatt) at an injection air temperature of 65-75° C. and an injection amount of 1-3 mL/min to obtain a imatinib-containing solid dispersion.

Preparation Example 14. Preparation of Solid Dispersion: Sorafenib

After dissolving 2.67 g of sorafenib tosylate (crystalline type III) and 5.34 g of Eudragit E 100 in 150 ml of EtOH (37° C.), the mixture was distilled under reduced pressure using a rotary evaporator, and the solvent was completely removed using a vacuum pump. A solid dispersion of sorafenib tosylate and Eudragit E formed on the wall was obtained. The yield was 65%.

Preparation Example 15. Preparation of Solid Dispersion: Sorafenib

A solid dispersion was prepared by mixing 7.2 g of sorafenib tosylate type III, 1.8 g of hypromellose, 0.7 g of povidone, and 0.2 g of poloxamer. Then, 2.9 g of Eudragit E was mixed with the solid dispersion and sieved to prepare a sorafenib solid dispersion mixture.

Preparation Example 16. Preparation of Solid Dispersion: Sunitinib

After dissolving 4 g of sunitinib free base and 8 g of hypromellose in a mixed solvent of ethanol and water (ethanol:water=8:2), the mixture was distilled under reduced pressure using a rotary evaporator, and the solvent was completely removed using a vacuum pump. A solid dispersion formed on the wall was obtained.

Preparation Example 17. Preparation of Solid Dispersion: Dasatinib

After dissolving 6.2 g of dasatinib anhydride, 12.4 g of hypromellose and 0.62 g of Tween 80 in a mixed solvent of ethanol and water (ethanol:water=7:3), the mixture was distilled under reduced pressure using a rotary evaporator, and the solvent was completely removed using a vacuum pump. A solid dispersion formed on the wall was obtained.

Preparation Example 18. Preparation of Solid Dispersion: Pazopanib

After dissolving 10 g of pazopanib hydrochloride, 10 g of hypromellose and 1 g of Tween 80 in a mixed solvent of ethanol and water (ethanol:water=7:3), the mixture was distilled under reduced pressure using a rotary evaporator, and the solvent was completely removed using a vacuum pump. A solid dispersion formed on the wall was obtained.

Preparation Example 19. Preparation of Solid Dispersion: Lapatinib

After dissolving 10 g of lapatinib ditosylate, 10 g of hypromellose and 1 g of Tween 80 in a mixed solvent of ethanol and water (ethanol:water=7:3), the mixture was distilled under reduced pressure using a rotary evaporator, and the solvent was completely removed using a vacuum pump. A solid dispersion formed on the wall was obtained.

Preparation Example 20. Preparation of Solid Dispersion: Axitinib

After dissolving 3 g of axitinib and 4 g of hypromellose in a mixed solvent of ethanol and water (ethanol:water=7:3), the mixture was distilled under reduced pressure using a rotary evaporator, and the solvent was completely removed using a vacuum pump. A solid dispersion formed on the wall was obtained.

Preparation Example 21. Preparation of Solid Dispersion: Cabozantinib

After dissolving 3 g of cabozantinib malate, 3 g of hypromellose and 1 g of Tween 80 in a mixed solvent of ethanol and water (ethanol:water=7:3), the mixture was distilled under reduced pressure using a rotary evaporator, and the solvent was completely removed using a vacuum pump. A solid dispersion formed on the wall was obtained.

Preparation Example 22. Preparation of Solid Dispersion: Ponatinib

After dissolving 3 g of ponatinib and 6 g of hypromellose in a mixed solvent of ethanol and water (ethanol:water=7:3), the mixture was distilled under reduced pressure using a rotary evaporator, and the solvent was completely removed using a vacuum pump. A solid dispersion formed on the wall was obtained. The yield was 62%.

Preparation Example 23. Preparation of Solid Dispersion: Vandetanib

After dissolving 3.5 g of vandetanib and 3.5 g of hypromellose in a mixed solvent of ethanol and water (ethanol:water=8:2), the mixture was distilled under reduced pressure using a rotary evaporator, and the solvent was completely removed using a vacuum pump. A solid dispersion formed on the wall was obtained.

Preparation Example 24. Preparation of a Solid Dispersion: Nilotinib

After dissolving 3 g of nilotinib hydrochloride, 6 g of hypromellose and 0.5 g of Tween 80 in a mixed solvent of ethanol and water (ethanol:water=7:3), the mixture was distilled under reduced pressure using a rotary evaporator, and the solvent was completely removed using a vacuum pump. A solid dispersion formed on the wall was obtained.

Preparation Example 25. Preparation of Solid Dispersion: Everolimus

After dissolving 3 g of everolimus and 9 g of hypromellose in a mixed solvent of ethanol and water (ethanol:water=8:2), the mixture was distilled under reduced pressure using a rotary evaporator, and the solvent was completely removed using a vacuum pump. A solid dispersion formed on the wall was obtained.

Example 1

12.8 g of the solid dispersion mixture obtained in Preparation Example 15, 3.4 g of mannitol, 0.8 g of sodium starch glycolate and 1.3 g of sodium bicarbonate were sieved and mixed, and then 0.1 g of magnesium stearate was sieved and added to perform final mixing. The mixture was compressed into tablets with an 11-mm round punch based on 350.0 mg weight per tablet.

Example 2

12.9 g of the solid dispersion mixture obtained in Preparation Example 15, 2.0 g of mannitol, 0.8 g of sodium starch glycolate and 2.6 g of sodium bicarbonate were sieved and mixed, and then 0.1 g of magnesium stearate was sieved and added to perform final mixing. The mixture was compressed into tablets with an 11-mm round punch based on 350.0 mg weight per tablet.

Example 3

12.9 g of the solid dispersion mixture obtained in Preparation Example 15, 1.5 g of mannitol, 0.8 g of sodium starch glycolate and 3.2 g of sodium bicarbonate were sieved and mixed, and then 0.1 g of magnesium stearate was sieved and added to perform final mixing. The mixture was compressed into tablets with an 11-mm round punch based on 350.0 mg weight per tablet.

Example 4

12.9 g of the solid dispersion mixture obtained in Preparation Example 15, 1.0 g of mannitol, 0.8 g of sodium starch glycolate and 3.7 g of sodium bicarbonate were sieved and mixed, and then 0.1 g of magnesium stearate was sieved and added to perform final mixing. The mixture was compressed into tablets with an 11-mm round punch based on 350.0 mg weight per tablet.

The composition of Examples by the sodium bicarbonate ratio is shown in Table 4 below.

TABLE 4

(unit: mg)

| | Component | Example 1 | Example 2 | Example 3 | Example 4 |
|---|---|---|---|---|---|
| Sorafenib solid dispersion | Sorafenib tosylate | 137.0 | 137.0 | 137.0 | 137.0 |
| | Hypromellose | 34.3 | 34.3 | 34.3 | 34.3 |
| | Povidone | 13.7 | 13.7 | 13.7 | 13.7 |
| | Poloxamer 407 | 4.1 | 4.1 | 4.1 | 4.1 |
| Tablet | Eudragit E | 54.8 | 54.8 | 54.8 | 54.8 |
| | Mannitol | 63.5 | 38.5 | 28.5 | 18.5 |
| | Sodium starch glycolate | 15.8 | 15.8 | 15.8 | 15.8 |
| | Sodium bicarbonate | 25.0 | 50.0 | 60.0 | 70.0 |
| | Magnesium stearate | 1.8 | 1.8 | 1.8 | 1.8 |
| | Total | 350 | 350 | 350 | 350 |

Examples 5-14

1.8 g of the solid dispersion mixture obtained in Preparation Examples 16-25, 1 g of mannitol, 0.3 g of sodium starch glycolate and 1 g of sodium bicarbonate were sieved and mixed, and then 0.05 g of magnesium stearate was sieved and added to perform final mixing. The mixture was manually compressed into tablets with an 8.5-mm round punch based on 200.0 mg weight per tablet.

The composition of components in tablet according to each Example is shown in Table 5 below.

TABLE 5

(unit: mg)

| | | Example | | | | | | | | | |
|---|---|---|---|---|---|---|---|---|---|---|---|
| | Component | 5 | 6 | 7 | 8 | 9 | 10 | 11 | 12 | 13 | 14 |
| Solid dispersion | Preparation Example | 16 | 17 | 18 | 19 | 20 | 21 | 22 | 23 | 24 | 25 |
| | API | 29.3 | 28.3 | 41.8 | 41.8 | 37.6 | 37.6 | 29.3 | 43.9 | 27.7 | 22.0 |
| | Hypromellose | 58.5 | 56.6 | 41.8 | 41.8 | 50.2 | 37.6 | 58.5 | 43.9 | 55.5 | 65.9 |
| | Tween 80 | — | 2.8 | 4.2 | 4.2 | — | 12.5 | — | — | 4.6 | — |
| Tablet | Mannitol | 48.8 | 48.8 | 48.8 | 48.8 | 48.8 | 48.8 | 48.8 | 48.8 | 48.8 | 48.8 |
| | Sodium starch glycolate | 12.2 | 12.2 | 12.2 | 12.2 | 12.2 | 12.2 | 12.2 | 12.2 | 12.2 | 12.2 |
| | Sodium bicarbonate | 48.8 | 48.8 | 48.8 | 48.8 | 48.8 | 48.8 | 48.8 | 48.8 | 48.8 | 48.8 |
| | Magnesium stearate | 2.4 | 2.4 | 2.4 | 2.4 | 2.4 | 2.4 | 2.4 | 2.4 | 2.4 | 2.4 |
| | Total | 200 | 200 | 200 | 200 | 200 | 200 | 200 | 200 | 200 | 200 |

Test Example 1: Measurement of Physical Properties of Tablets

[Friability Measurement]

Friability is a method described in the U.S. Pharmacopoeia 1216 Tablet Friability category, and was measured using a LABFINE friability tester on 10 tablets, and the results are shown in Table 6 below (measurement time=4 minutes).

TABLE 6

| | Friability |
|---|---|
| Example 1 | 0.11% |
| Example 2 | 0.11% |
| Example 3 | 0.19% |
| Example 4 | 0.36% |

TABLE 6-continued

| | Friability |
|---|---|
| Example 5 | 0.18% |
| Example 6 | 0.19% |
| Example 7 | 0.29% |
| Example 8 | 0.25% |
| Example 9 | 0.21% |
| Example 10 | 0.19% |
| Example 11 | 0.23% |
| Example 12 | 0.18% |
| Example 13 | 0.26% |
| Example 14 | 0.30% |

[Disintegration Test]

According to the disintegration test method of the 10th revision of the Korean Pharmacopoeia General Test, disintegration test was performed in a solution of pH 1.2 with n=3 for each Example, and the results are shown in Table 7 below.

TABLE 7

| | Disintegration time |
|---|---|
| Example 1 | 35 minutes 10 seconds |
| Example 2 | 4 minutes 58 seconds |
| Example 3 | 5 minutes 55 seconds |
| Example 4 | 5 minutes 52 seconds |
| Example 5 | 4 minutes 34 seconds |
| Example 6 | 4 minutes 30 seconds |
| Example 7 | 5 minutes 35 seconds |
| Example 8 | 3 minutes 49 seconds |
| Example 9 | 4 minutes 07 seconds |
| Example 10 | 5 minutes 00 seconds |
| Example 11 | 4 minutes 20 seconds |
| Example 12 | 4 minutes 50 seconds |
| Example 13 | 5 minutes 05 seconds |
| Example 14 | 5 minutes 12 seconds |

The invention claimed is:

1. An oral solid formulation composition comprising
a mixture comprising an active ingredient and a water-soluble or gastric-soluble polymer as a solubilizing carrier, and a foaming component as a disintegration promoter,
wherein the foaming component comprises a foaming agent and does not comprise an acidifying agent;
the active ingredient is selected from the group consisting of sorafenib tosylate, lapatinib ditosylate, dasatinib anhydride, nilotinib hydrochloride monohydrate, cabozantinib malate, and ponatinib hydrochloride hydrate;
the water-soluble or gastric-soluble polymer is a mixture of hypromellose and Eudragit E in a weight ratio of 0.62-0.63:1;
the active ingredient is comprised in an amount of 35 to 45% by weight based on a total weight of the composition;
the water-soluble or gastric-soluble polymer is comprised in an amount of 23 to 28% by weight based on the total weight of the composition; and
the foaming agent is comprised in an amount of 25 to 35 parts by weight based on 100 parts by weight of the water-soluble or gastric-soluble polymer.

2. The oral solid formulation composition according to claim 1, wherein the mixture is in the form of a solid dispersion.

3. The oral solid formulation composition according to claim 1, further comprising a dissolution aid.

4. The oral solid formulation composition according to claim 3, comprising a polymethacrylate copolymer as a dissolution aid.

5. A method for preparing an oral solid formulation composition comprising:
(1) a step of preparing a mixture comprising an active ingredient and a water-soluble or gastric-soluble polymer as a solubilizing carrier; and
(2) a step of adding a foaming component as a disintegration promoter to the mixture,
wherein the foaming component comprises a foaming agent and does not comprise an acidifying agent;
the active ingredient is selected from the group consisting of sorafenib tosylate, lapatinib ditosylate, dasatinib anhydride, nilotinib hydrochloride monohydrate, cabozantinib malate, and ponatinib hydrochloride hydrate;
the water-soluble or gastric-soluble polymer is a mixture of hypromellose and Eudragit E in a weight ratio of 0.62-0.63:1;
the active ingredient is comprised in an amount of 35 to 45% by weight based on a total weight of the composition;
the water-soluble or gastric-soluble polymer is comprised in an amount of 23 to 28% by weight based on the total weight of the composition; and
the foaming agent is comprised in an amount of 25 to 35 parts by weight based on 100 parts by weight of the water-soluble or gastric-soluble polymer.

6. The oral solid formulation composition according to claim 1, wherein the active ingredient is selected from the group consisting of lapatinib ditosylate, dasatinib anhydride, nilotinib hydrochloride monohydrate, cabozantinib malate, and ponatinib hydrochloride hydrate.

7. The oral solid formulation composition according to claim 1, wherein the amount of the active ingredient is 39 to 40% by weight based on the total weight of the composition;
the amount of the water-soluble or gastric-soluble polymer is 25 to 26% by weight based on the total weight of the composition; and
the amount of the foaming agent is 28 to 29 parts by weight based on 100 parts by weight of the water-soluble or gastric-soluble polymer.

8. The oral solid formulation composition according to claim 1, wherein the mixture of the water-soluble or gastric-soluble polymer comprises hypromellose in an amount of 34.3 mg and Eudragit E in an amount of 54.8 mg;
the amount of the active ingredient is 137 mg;
the amount of the foaming agent is 25 mg; and
the total weight of the composition is 350 mg.

9. The oral solid formulation composition according to claim 1, wherein the active ingredient has a dissolution rate in the composition after 30 minutes of 81.0 to 99.2%, the dissolution rate being measured according to the paddle method of dissolution test in Korean Pharmacopoeia using 900 mL of pH 1.2 buffer solution at 100 rotations per minute, and a filter paper with a pore size of 0.45 µm, followed by high performance liquid chromatography.

10. The oral solid formulation composition according to claim 1, wherein the foaming agent is sodium bicarbonate.

* * * * *